US006190665B1

(12) United States Patent
Inoue et al.

(10) Patent No.: US 6,190,665 B1
(45) Date of Patent: Feb. 20, 2001

(54) CALCIUM CHANNEL ANTAGONIST POSSESSING AN INHIBITORY ACTION AGAINST SECRETION OF PARATHYROID HORMONES AND A USE THEREOF

(75) Inventors: Ranko Inoue; Takeshi Inoue, both of Tokyo; Takuo Fujita, Kobe; Yoshihisa Kudoh, Machida; Seiichi Yamagiwa, Tokyo, all of (JP)

(73) Assignee: Fujix Inc., Tokyo (JP)

( * ) Notice: Under 35 U.S.C. 154(b), the term of this patent shall be extended for 0 days.

(21) Appl. No.: 09/081,055

(22) Filed: May 19, 1998

(30) Foreign Application Priority Data

May 21, 1997 (JP) .................................................. 9-130907

(51) Int. Cl.[7] .................................................. A01N 65/00
(52) U.S. Cl. .............................................. 424/195.1
(58) Field of Search .......................................... 424/195.1

(56) References Cited

FOREIGN PATENT DOCUMENTS

404173061 * 6/1992 (JP) .

OTHER PUBLICATIONS

Biosis Computer Abstract 1978:130112 Bradfield "Extraction of Calcium Fractions from Plant Material" Commun Soil Sci Plant Anal (1977) 8 (7) 563–572.*

Scisearch Computer Abstract 91:659605 Clark et al "Seasonal Changes in the Form and Districturion of Calcium in Fruit of Kiwifruit Vines" Jour Hort. Science (1991) V 66 No. 6 pp.747–753, 1977.*

Fujita et al. Miner. Electrolyte Metab. (1995) 21: 299–231.*

Fujita, T. J. Bone Miner. Metab. (1996) 14: 31–34.*

Fujita et al. Calcif. Tissue Int. (1996) 58: 226–230.*

* cited by examiner

*Primary Examiner*—Herbert J. Lilling
(74) *Attorney, Agent, or Firm*—Armstrong, Westerman, Hattori, McLeland & Naughton

(57) ABSTRACT

Disclosed is a calcium channel antagonist effective as a single substance for attaining dual purposes of inhibiting secretion of parathyroid hormones and of promoting absorption and utilization of calcium in human body as well as a process for preparing the calcium channel antagonist. According to the present invention. the calcium channel antagonist is prepared by baking a calciferous material of plant origin at a temperature of 500–1000° C. under reduce pressure or vacuum and extracting the baked material with and acidic substance. The calcium channel antagonist may be incorporated with a conventional calcium preparations to enhance bioavailability of calcium. Further, the calcium channel antagonist of the present invention may be processed to calcium preparations in the form of porous granules.

3 Claims, 8 Drawing Sheets

CALCIUM CHANNEL ANTAGONIST POSSESSING AN INHIBITORY ACTION AGAINST SECRETION OF PARATHYROID HORMONES AND A USE THEREOF

BACKGROUND OF THE INVENTION

1. Field of the Invention

The present invention relates to a calcium channel antagonist capable of inhibiting intrusion of calcium into cells which possesses an inhibitory action against secretion of parathyroid hormones, an agent (a medicament) for promoting absorption and utlization of calcium into human body as well as a process for preparing the antagonist and the agent and also to a calcium preparation wherein a calcium material has been incorporated with the calcium channel antagonist for enhancing effective utilization of the calcium value. More particularly, the present invention relate to a calcium channel antagonist possessing an inhibitory action against secretion of parathyroid hormones which comprises an acid extract of a calciferous (calcium-containing) material of plant origin baked in a specific manner, an agent (medicament) for promoting absorption and utilization of calcium as well as a process for preparation thereof, and a calcium preparation wherein a known calcium preparation has been incorporated with the calcium channel antagonist.

As is evident from the foregoing description, the calcium channel antagonist of the present invention is effective as a single substance for attaining dual purpose of inhibiting secretion of parathyroid hormones and promoting absorption and utilization of calcium in human body.

2. Description of the Prior Art

It is well recognized that calcium is one of the indispensable constituents for the formation of bones and teeth of mammalia including human. In recent years, it has become manifested, not only the above recognition, that calcium is one of the most important nutritive substances sustaining all of the living phenomena. Accordingly, calcium is now being watched among research staffs in the far front of the medical field.

As an example of this fact, a variety of studies on calcium paradox are reported under the title of "Contact Point of Dietetics with Cytobiology" in a Japanese magazine entitled "Clinical Calcium", Special Edition, 'Calcium Paradox', January 1996 published by Medicinal Journal Co.

According to these medical articles, a great number of functions attained by calcium in human body have been made clear. Above all, a key of human health has now become impossible to consider without the relation between calcium and parathyroid hormones.

Reported heretofore is that the living action of human including digestion, absorption and excretion of foods; synthesis and internal secretion of hormones; immunization mechanism; function of looking at everything; function of thinking about everything; and other all functions depends on the action of calcium in such manner that all of the cells are controlled by the signal (information) emitted from calcium in blood and working of heart and brain is caused by the action of calcium.

According to this report, it is necessary that the concentration of calcium in blood has to be maintained at all times at a definite level in order that cells may function normally. It has also been made clear that a difference in concentration of calcium between the inside and outside of cells (in blood) has to be maintained at about 1:10,000.

To say it in another way, the concentration of calcium inside cells has to be kept at 1/10,000 of that outside cells in order that the signal emitted from calcium may correctly be caught. So far as the difference in concentration is kept, the individual cells can act their rolls according to the correctly transmitted information.

In case the concentration of calcium in blood is decreased, working of heart and brain will be ceased to cause death. In order to prevent such deleterious or rather fatal result, human body is naturally designed to have parathyroid hormones worked for dissolving calcium from bones into blood to maintain life. In human body, 99% of calcium is stored in bones. If dissolution of calcium from bones continues and goes too far, solid bones will become spongy to cause osteoporosis. What is more, continuous dissolution of calcium incurs a detrimental influence on human body in that although action of heart is not ceased and life is thus maintained by augmenting blood with calcium, excess calcium brought over in cells by internal secretion of parathyroid hormones incurs considerable overbalance of calcium concentration inside and outside the cells, thus disturbing intercellular transmission of information to lose normal action of the cells. This phenomenon is called calcium paradox which is a disease caused by a series of phenomena; (I) shortage of calcium, (II) depression of calcium concentration in blood, and (III) secretion of parathyroid hormones capable of increasing calcium in cells. This calcium paradox exhibits the following symptoms: headache, dementia, cataract, anemia, hypertension/apoplexy, deafness, hypotension, stiff shoulder, immunodeficiency, osteoporosis, stress, arterosclerosis/cardiac infarctio, gastric ulcer, duodenal ulcer, infectios disease/cold, pneumonia, cancer, allergy/atopy, renal calculus, prostatomegaly, weak nail, hepatitis/cirrhosis, neuralgia, chronic articular rheumatism, and arthritis By increase of calcium in cells is meant that the cells get ill and go to aging. If calcium is continuously increased, cells sustaining life will decease, inducing death of human life as a matter of course.

For human body consisting of about 60 trillion cells, calcium is one of the indispensable nutrients sustaining not only bones but also living action of all tissues including heart and brain and always has to be supplemented externally as an important nutritive component lest it should become short.

Notwithstanding calcium is such an important nutritive component, it is a current status that our dietary life is recently dependent on processed foods and our intake ratio of calcium is not said to be sufficient.

In the event foods is short of calcium, the content of calcium in body becomes smaller and moreover a balance of calcium saved at a definite rate in cells, blood, and bones will be lost so that the aforesaid considerable status for human body will be incurred.

A preferable ratio of calcium existing in cells, blood and bones is said to be about 1:10,000:100,000,000. Calcium existing in such ratio in cells, blood and bones displays respectively the following behavior:

The actions of calcium in cells are: (i) sustaining whatever actions in cells and receiving information, and (ii) causing cleavage, multiplication, movement, secretion, excitement, and metabolism of cells.

In blood, calcium exists in an amount of 10,000 times of the cells and displays the following behavior: (i) activating heart and brain, controlling the action of cells and receiving information; (ii) transporting calcium everywhere in body, and (iii) maintaining calcium in blood at all time at a definite concentration.

A calcium value saved in bones occupies 99% of the total calcium and displays the following behavior: (i) supporting body and making bones strong, and (ii) in case of the calcium concentration in blood being decreased, dissolving calcium from bones by the aid of parathyroid hormones thereby supplementing the lacked portion and maintaining calcium in blood at a definite concentration.

Problems to be Solved by the Invention

As is understood from the foregoing, if calcium in an amount sufficient enough to maintain calcium in blood at a definite concentration is at all times supplemented externally, secretion of parathyroid hormones fails to take place so that calcium is not increased in cells to ensure that all of the functions in human body act normally.

According to the recent study, an amount of calcium daily necessary for adult is reported as 800 mg. Noteworthy here is, however, that all of the calcium contained in foods and drinks is not absorbed in human body. It has now been made clear that the calcium content usually designated for foods and drinks is greatly different from the amount of calcium actually absorbed in human body. It follows that if a necessary amount of calcium is to be taken from daily meals, an enormous amount of calciferous foods will have to be taken.

For example, a calcium content of milk known as a drink containing a high unit of calcium is at most about 100 mg/100 ml. As the calcium contained in milk is combined with proteins, its absorbability is said to be good. However, absorption rate of calcium for human body is 50% in maximum, i.e. only 50 mg of calcium is absorbable per 100 ml of milk. Furthermore, proteins present in milk as a combined state with calcium are digested, absorbed and finally converted into acids such as lactic acid, butyric acid, pyruvic acid, sulfuric acid, and phosphoric acid so that a majority of the aforesaid 50 mg of calcium may be consumed to neutralize these acids. Thus, notice has to be paid to a report that a calcium value in 100 ml of milk absorbed in human body may actually be at most about 20 mg. It is a matter of course, therefore, that a necessary amount of calcium cannot be supplemented only with milk. In case an insufficient amount of calcium is to be supplemented with other food and drinks, the amount of calcium contained in such foods and drinks, even in case of dried sardines, fresh sardines, hijiki (*Hijikiaf fucales*—a kind of sea weed), and baked laver are known as calcium-enriched foods, is smaller and utterly fails to reach the above mentioned daily necessary amount. After all, it is a current status that intake of a necessary amount of calcium is rather hard from usual meals. Consequently, we gradually fall in the state of chronic short of calcium, thus incurring a recurring phenomena of decrease in calcium concentration in blood, secretion of parathyroid hormones for compensation of the decreased amount of calcium, and a continuous dissolution of calcium from bones causing the aforesaid various diseases.

Such status is not limited to our country, especially in view of the fact that even in European and American countries where consumption of milk is said to be 3–5 times as much as our country, osteoporosis patients caused by short of calcium in these countries are twice in number as compared with those in our country. In view of this fact, it will easily be understood that solution of the problem of calcium deficiency is impossible only by intake of a calcium-enriched foods and drinks such as milk.

As for Vitamin D known as promoting absorption of calcium, this vitamin can be formed by sunlight irradiation of a provitamin D in body or can be taken from foods. Vitamin D is converted by the aid of liver or kidney into an active type Vitamin D which assists absorption of calcium through intestine. However, this function is extremely decreased as aging proceeds. Further, intake of synthetic active type Vitamin D brings about a problem as it accompanies a considerable side-effect of causing hypercalcemia, uremia, and osteomalacia.

SUMMARY OF THE INVENTION

Accordingly, it is an object of the present invention to provide a calcium channel antagonist capable of inhibiting secretion of parathyroid hormones and intrusion of calcium into cells, and simultaneously effective for promoting absorption and utilization of calcium, as well as a process for preparing same.

It is another object of the present invention to provide a calcium preparation capable of being added to calcium or conventional calcium preparations, which preparation can be enhanced in absorption efficiency of calcium without assistance of Vitamin D, any athletic movement and irradiation of sunlight and is effective for the formation of bones without exhibiting any side-effect because of its extremely high in vivo utilization efficiency (or bioavailability) of absorbed calcium.

DETAILED DESCRIPTION OF PREFERRED EMBODIMENTS OF THE INVENTION

Means for Solving the Problems

Figure 1:
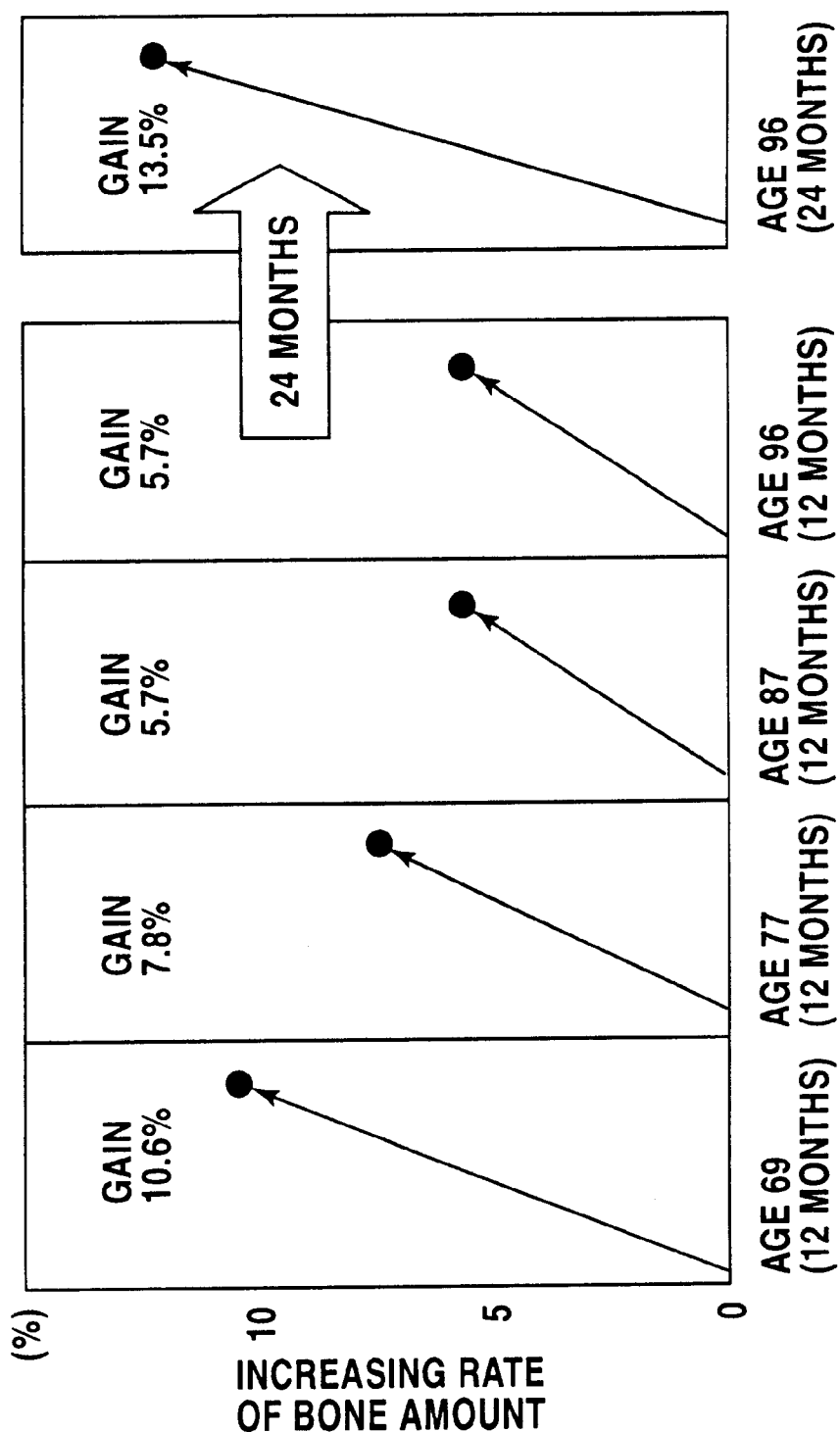
FIG. 1 is a drawing showing change of bone amount according to Example 1.
Figure 2:
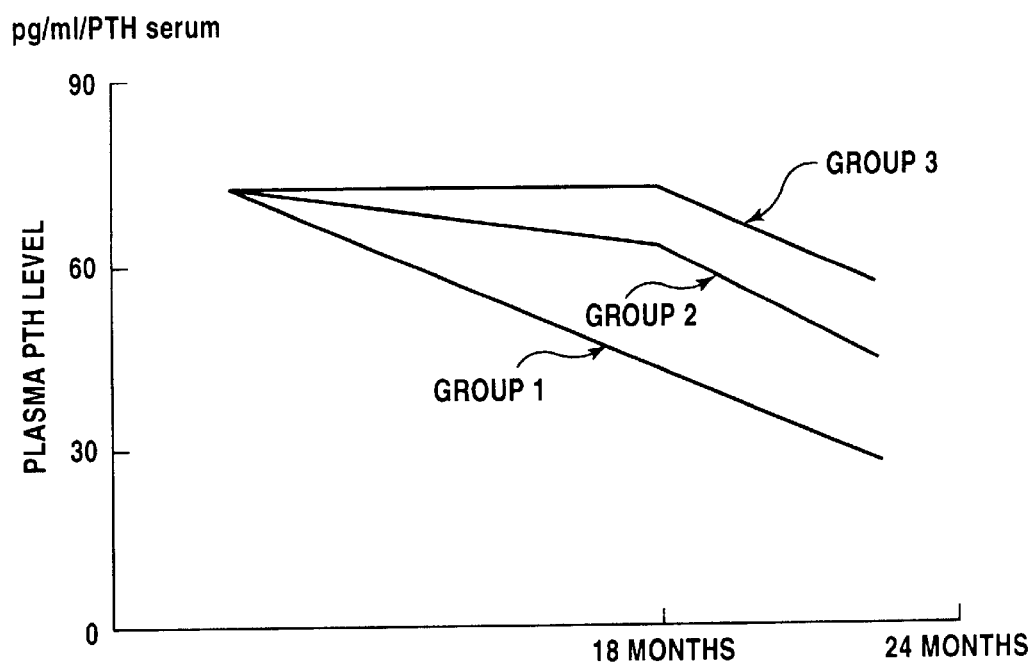
FIG. 2 is a drawing showing a secretion-inhibiting effect of PTH according to Example 2.

The present invention has been proposed for achieving the above objects and comprises as a fundamental invention a calcium channel antagonist effective for dual purpose of promoting absorption and utilization of calcium, and of inhibiting secretion of parathyroid hormones, which comprises an acid extract of a baked calciferous material of plant origin according to a specific method as well as a process for preparing same, and as a second invention a calcium preparation which comprises the aforesaid calcium channel antagonist incorporated with calcium or known conventional calcium preparations.

In accordance with the present invention, there is provided a calcium channel antagonist effective for dual purpose of inhibiting secretion of parathyroid hormones and of promoting absorption and utilization of calcium, which comprises an acid extract of a calciferous material of plant origin.

In accordance with the present invention, there is also provided the aforesaid calcium channel antagonist wherein the calciferous material of plant origin is at least one selected from the group consisting of sea weeds, beans, grasses belonging to Graminaceae, sesame, tea, mineral-containing plants, and carbonized plants.

In accordance with the present invention, there is further provided the aforesaid calcium channel antagonist wherein baking of the calciferous material has been effected under reduced pressure or vacuum.

In accordance with the present invention, there is still further provided the aforesaid calcium channel antagonist wherein the acid extract obtained after baking of the calciferous material is prepared by treating the baked calciferous material with a strong acid and diluting the extract with an almost same amount of water.

In accordance with the present invention, there is still further provided a calcium preparation enhanced in bioavailability, wherein a calcium material has been incorporated with the calcium channel antagonist.

In accordance with the present invention, there is still further provided the aforesaid calcium preparation wherein the calcium material has been obtained by baking a calciferous material of plant or animal origin.

In accordance with the present invention, there is still further provided the aforesaid calcium preparation, wherein it has been processed to porous powders by subjecting the calcium preparation to spray drying.

In accordance with the present invention, there is still further provided a process for preparing the aforesaid calcium channel antagonist, which comprises baking a calciferous material of plant origin under reduced pressure or vacuum at a temperature of 300–1000° C. and soaking the baked material in a strong acid for extraction.

In accordance with the present invention, there is still further provided a process for preparing the aforesaid calcium channel antagonist, wherein the baking of the calciferous material is carried out at a temperature of 500–1000° C. under reduced pressure or vacuum.

In accordance with the present invention, there is yet further provided a process for preparing the aforesaid calcium channel antagonist, wherein the baked material is soaked in a strong acid and an acid extract is diluted with an almost same amount of water.

Modes of Carrying out the Invention

An important feature of the present invention was to find that a product obtained by baking a calciferous material of plant origin according to a specific method and extracting the baked material with an acid according to a specific method possesses an inhibitory action against secretion of parathyroid hormones and an extremely strong calcium channel antagonistic action exhibits very strong calcium channel antagonistic action in combination with an excellent absorption-promoting effect when added to known conventional calcium preparations.

The calcium channel antagonist effective also as the calcium preparation thus obtained in the present invention exhibits, unlike the conventional calcium preparations, an extremely high absorption-promoting effect only by oral administration without the aid of a conjoint use of Vitamin D or sunlight so that the absorbed calcium may effectively be utilized in vivo. Thus, an extremely outstanding effect is shown in the formation of bones for not only people of young generation but also people of senior ages.

Calcium Channel Antagonist also Effective as an Agent for Promoting Absorption and Utilization of Calcium Utilizable as starting material for the calcium channel antagonist (also effective as an agent for promoting absorption and utilization of calcium) of the present invention are calciferous materials of plant origin selected from the group consisting of sea weeds, beans, grasses belonging to Graminaceae, sesame, tea, minerals-containing plants, and carbonized plants. Illustrative of the calciferous material are, for example, sea weeds such as hijiki, beans such as soy bean, red bean, etc., Graminaceae plants such as wheat, bamboo grass, etc., sesame, various kinds of tea, mineral-containing plants and carbonized plants such as lignite. These materials may be used singly or in a mixture of at lest two.

In the present invention, the aforesaid starting material is baked under reduced pressure or vacuum and then extracted with an acid. Among the starting materials, a calcium-enriched hijiki is preferably used.

A baking treatment of the starting material is preferably carried out while intercepting air (oxygen). Although the baking condition varies according to the sort of starting material, the baking temperature is usually 500–1000° C., preferably 700–800° C., and more preferably 730–760° C., for example, in case of hijiki. The baking time varies according to the amount and sort of the starting material, but usually a period of about one hour is sufficient.

In the present invention, it is of importance that the baked or calcine material is subjected to extraction with an acid. Especially preferable as the acid in this case are strong acids such as sulfuric acid and pineapple enzyme. The extraction treatment of the baked material with the acid is generally carried out by soaking the baked material in the acid for about 24 hours, After completion of the extract treatment, water is added to the acid extract to form an aqueous solution thereof. No limitation exists in the quantity of water to be added. In general, however, it is preferable to use water in an amount of 1–3 times as much as the amount of the acid extract. It is more preferable to use water in the same amount as the acid extract.

An aqueous solution of the acid extract thus obtained is referred to herein arbitrarily as "HAI" which is an abbreviation of Heat Alge Ingredient. HAI itself exhibits an excellent effect as calcium channel antagonist. By the term "calcium channel antagonist" is meant herein an agent (medicament) possessing an inhibitory action against intrusion of calcium into cells.

If the concentration of calcium in blood is decreased due to short of calcium, secretion of parathyroid hormones will take place, as described hereinbefore, according to the mechanism in vivo for maintenance of life whereby calcium saved in bones are dissolved in blood to keep balance of the concentration. As will be evident from Examples 4 given hereinafter, parathyroid hormones also function to bring over excess calcium into cells so that calcium dissolved from bones may intrude into cells to increase the calcium concentration in the cells. In case the concentration of calcium in cells is increased, health is break down to induce various lesions. For example, vessels are shrinked to cause arterial sclerosis, thus resulting in death of brain cells and other cells. For preventing various diseases caused by overbalance of calcium, a study for effective calcium channel antagonists is now being watched.

In the field of calcium channel antagonists, however, it is a current status that an excellent medicament has not yet been found and a few synthetic medicaments now developed exhibit more or less harmful side-effects.

Concerning this point, an interesting study was reported in The 17th American Society for Bone Metabolism held in 1995 (September), which is suggestive of that the mortality rate of ladies continuing supplement of calcium is low. According to this report, ladies having a low parathyroid hormones level (20 units/di or less) are 69% lower in the total mortality rate than those having a higher hormones level. In addition, this report gives a notice that ladies receiving supplement of calcium are 18% lower in mortality rate than those not receiving supplement of calcium and that ladies receiving supplement of calcium are lower in lower in parathyroid hormones level in blood and in mortality rate than those not receiving supplement of calcium.

In order to stop a vicious circle of (i) short of calcium, (ii) secretion of parathyroid hormones and (iii) intrusion of calcium into cells, it is important as a primary step that short of calcium does not take place in vivo. Even if secretion from parathyroid gland takes place, a calcium channel antagonistic effect is quite indispensable to prevent intrusion of calcium into cells.

The main ingredient HAI of the present invention are all plant origin and is prepared by baking followed by acid extraction. Thus, this substance has no harmful side-effect to human body. In addition, HAI has an inhibitory action against secretion of parathyroid hormones so that intrusion of calcium into cells can entirely be prevented as calcium channel antagonistic effect.

It has now been made clear that when HAI of the present invention is added to a conventional calcium preparation, absorption of calcium into human body is markedly enhanced. Thus, HAI of the present invention attains dual effect for maintaining life; (i) inhibiting secretion of parathyroid hormones to prevent intrusion of calcium into cells and (ii) extremely enhancing absorption of calcium into human body when added to a conventional calcium preparation. Calcium thus absorbed in body exhibits an excellent result for the formation of bones. It is a matter of course that a conventional calcium preparation incorporated with HAI of the present invention exhibits excellent absorbability of calcium and at the same time functions as a calcium channel antagonist.

Calcium Preparations

Any of the conventional calcium preparations can freely be used as calcium value into which HAI of the present invention is to be incorporated. A baked material of a calciferous material of plant or animal origin also proposed by the inventors (Examples of Japanese Laid-open Patent Appln. No. Hei. 5-161480 referred to) is preferably used.

Porous Calcium Preparations

The aforesaid calcium preparations or those incorporated with HAI can be processed to a granulated product by dissolving the preparations in an organic acid or an organic acid-containing liquid and subjecting the solution to spray-drying to evaporate water. Illustrative of the organic acid for dissolving the calcium preparation are, for example, fermented lactic acid, citric acid, malic acid, acetic acid, etc. and a liquid containing these organic acid or acids.

Examples of the organic acid-containing liquid include squeezed fruit juices (organic acid or acids-containing liquids) such as papaya juice. In view of solubility of calcium and taste of the resultant granules, those containing lactic acid as main ingredient and pineapple juice are most preferably used.

Pulverization of Calcium-Containing Liquid

Solubility of calcium varies according to the sort of organic acids. If calcium forms a homogeneous solution irrespective of solubility, a water-soluble powdery substance wherein calcium is combined with organic acids can easily be prepared therefrom by merely evaporating water from the solution. As any unpleasant odor or taste are removed at the time of spray-drying, the resultant water-soluble powdery substance containing calcium has a mild fruit flavor and is easily ionized in water to enhance absorption and bioavailability of calcium.

In case spray-drying has to be carried out, a binder may optionally be used to facilitate agglomeration of powder. Examples of the utilizable binder include dextrin, CMC and MC. Ascorbic acid, fructose and the like may also be used optionally. In case a binder is not used, the granular size of the product is about 0.005–0.02 mm. By using a binder, the product having a larger granular size can easily be prepared.

An organic acid solution of calcium, for example, a juice containing calcium together with organic acids can be processed to porous, almost spherical granules since sugars contained in the juice functions as a binder. The product obtained by spray-drying is porous and almost spherical and so is distinguished by its superior solubility in water.

EXAMPLES

The present invention will now be illustrated by way of Examples and Referential Examples.

Referential Example 1

Preparation of Calcium Channel Antagonist

In a tray of a vacuum furnace provided with a heating device was placed 1 kg of dried hijiki, which was then baked for about 1hour at 750° C. under pressure of $2 \times 10^{-2}$ Torr. The resultant baked material was dipped in 2.6 liters of concentrated sulfuric acid for 24 hours to effect acid extraction. The resultant extract was filtered and diluted with about 2.6 liters of water to obtain a product (HAI) of about 5 liters.

Referential Example 2

Preparation of a Calcium Preparation

Oyster shell was thoroughly washed and darkened portions were removed. Oyster shell was then crushed to have a size of 5 cm×5 cm by the aid of a crusher. About 8 kg of the crushed oyster shell was placed on a titanium tray having a size of 50 cm×50 cm×50 cm and baked for 1 hour at 950° C. by the aid of an electric furnace. The baked shell was pulverized by the aid of a colloid mill to obtain calcium oxide (Calcium powder A) having an average particle size of 200 mesh as a white powder.

Referential Example 3
Granulation by Spray-Dryer

The aforesaid Calcium Powder A in an amount of 100 parts by weight was mixed with papaya juice in an amount of 900 parts by weight at room temperature. By gradually heating the mixture, the mixture formed a solution at about 70° C. This calcium solution was filtered while warming it at 75±° C. and the filtrate was supplied to a spray-dryer for granulation whereby porous spherical powdery granules having an average particle diameter of 7 μ were obtained.

This powdery product was palatable and its taste was mild acidic. The product was rapidly dissolved up to 3000 mg in 100 cc of water to form a transparent solution.

Example 1

HAI liquid (1 g) was added to 500 g of Calcium Powder A and the mixture was subjected to spray-drying for granulation in the same manner as above. The resultant product will be referred to hereinafter as "sample".

The sample was continuously administered to senior persons of an average age of 82 (3 persons) in a dose of 900 mg/day for 12 months. The sample was further administered to a person of age 96 for further 12 months. A change in bone amount of the test persons was measured and a result of the measurement is shown in Table 1. It was confirmed from the test that the sample promoted absorption of calcium and the bone amount was extremely increased.

Example 2

In the same manner as described in Example 1, the sample was continuously administered to senior persons of an average age of 82 (the first group) in a dose of 900 mg/day for 18 months. Next, the level of parathyroid hormones (PTH) was measured by way of plasma (pg/ml/PTH).

For comparison, calcium carbonate was continuously administered to three hospitalized patients of the second group (an average age of 81) in a dose of 900 mg/day, a placebo (a meal corresponding to calcium 600 mg/day) was continuously administered to three hospitalized patients of the third group (an average age of 84). After the lapse of 18 months, the PTH level (pg/ml/PTH) of each group was measured by way of plasma.

Table 2 shows the results of measurement for each group.

It was confirmed that the first group to which the sample had been administered was excellent in inhibitory action against secretion of PTH as compared with the second and third groups.

Example 3

Figure 3:
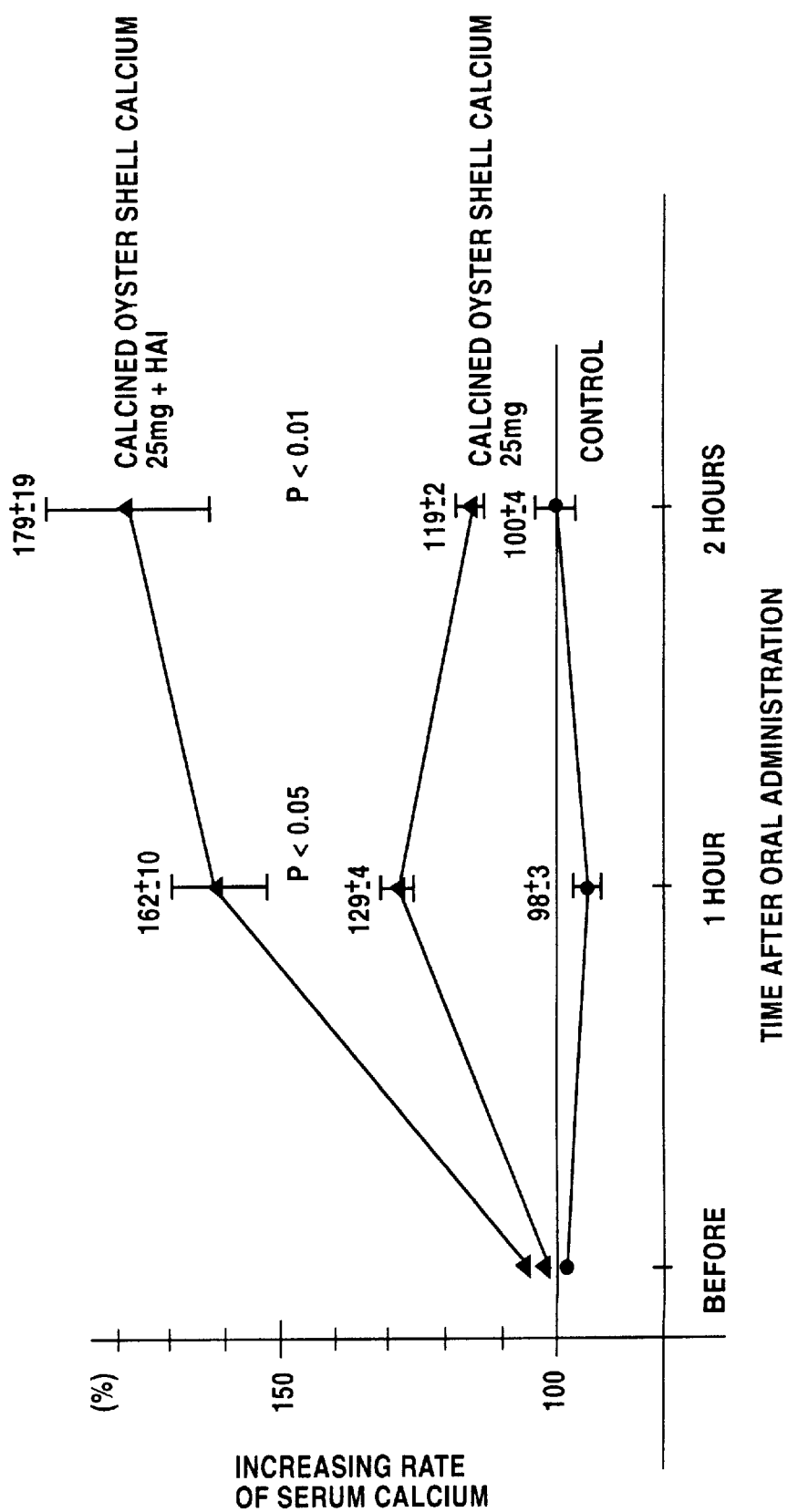
FIG. 3 is a graph showing a test result on an intestinal absorption effect of calcium in a parathyroid gland-excised rat according to Example 3.
Figure 4:
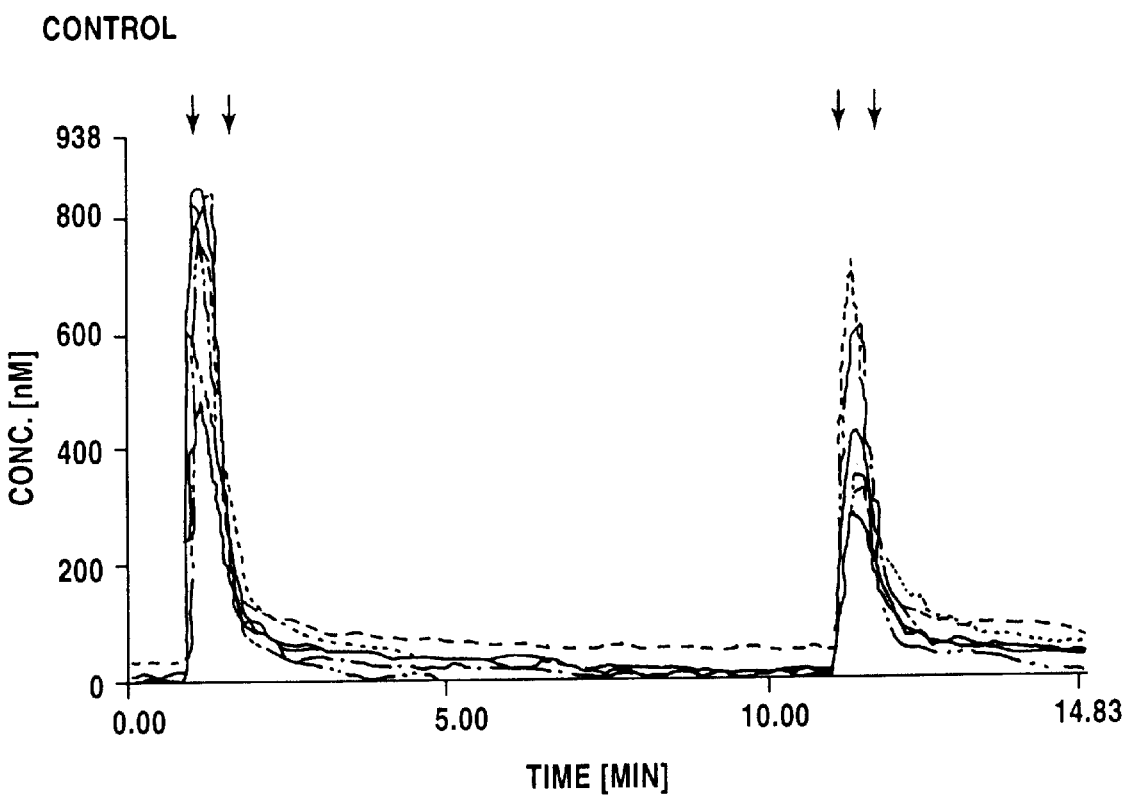
FIG. 4 is a graph showing the state of intruding calcium into cultured hippocampus cells of a rat without using HAI

The sample (25 mg) obtained in Example 1 was orally administered to a parathyroid gland-excised rat and an intestinal absorption effect was tested after the lapse of 1 hour and 2 hours. For comparison, a similar test was carried out for (1) oral administration of the baked oyster shell calcium obtained in Referential Example 2 and (2) nothing was administered. A result of the tests are shown in FIG. 3.

Example 4

A HAI solution obtained in Referential Example 1 was adjusted so as to have concentrations of 1/100, 1/1,000, 1/3,000 and 1/5,000. Using these HAI solutions and control, the calcium channel antagonistic tests were carried out in accordance with the following method and the test result were shown in FIGS. 4–8.

This test was made to study the effect of the HAI solutions on rapid increase of calcium concentration in the cell when a potential-dependent calcium channel is opened by applying a 50 mM isotonic KCl solution to cultured hippocampus cells.

This test was carried out in each case using the 10 cells. Almost all cases showed a similar result. Among them, the chart of 7 examples were shown in the drawings In FIG. 4 where the test result of control is shown, the application of KCl for 30 seconds was carried out twice at a time interval of 10 minutes. The second reaction was decided as a control reaction after the application of HAI.

Figure 5:
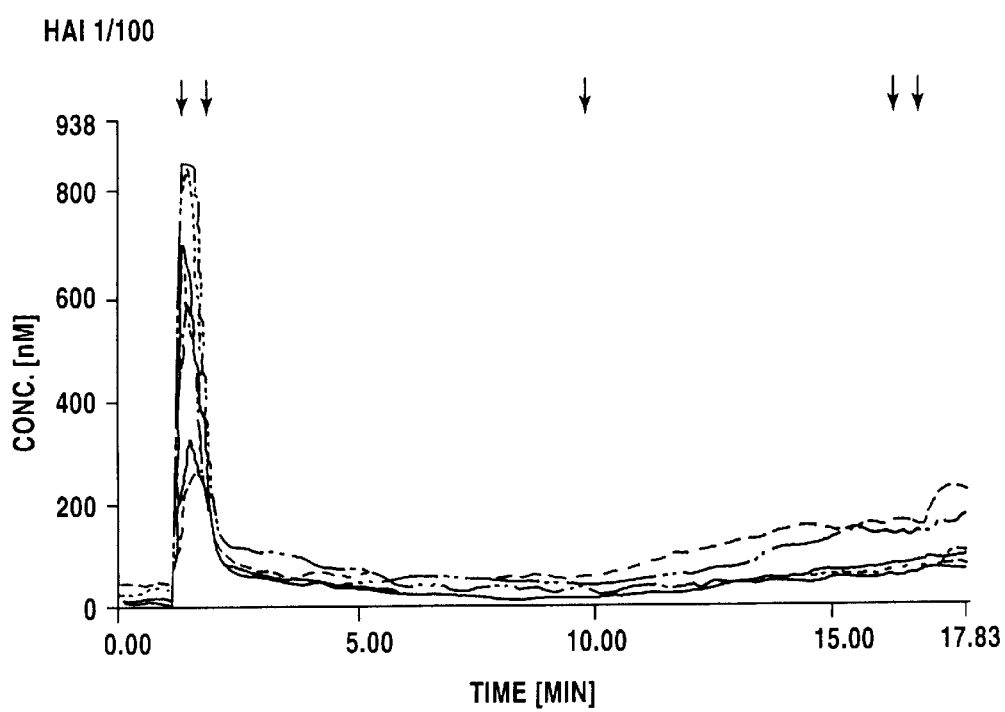
FIG. 5 is a graph showing the state of intruding calcium into cultured hippocampus cells of a rat with a 1/100 solution of HAI for proving the effect of calcium channel antagonist.

In FIG. 5, the diluted 1/100 HAI solution was given to the cells between the first application of KCl and the second application of KCl. The second application of KCl was made in the presence of the diluted 1/100 HAI solution. The increase of the calcium concentration by the second application of KCl was almost suppressed. An average reaction with 10 cells in total was around 25% of the control.

Figure 6:
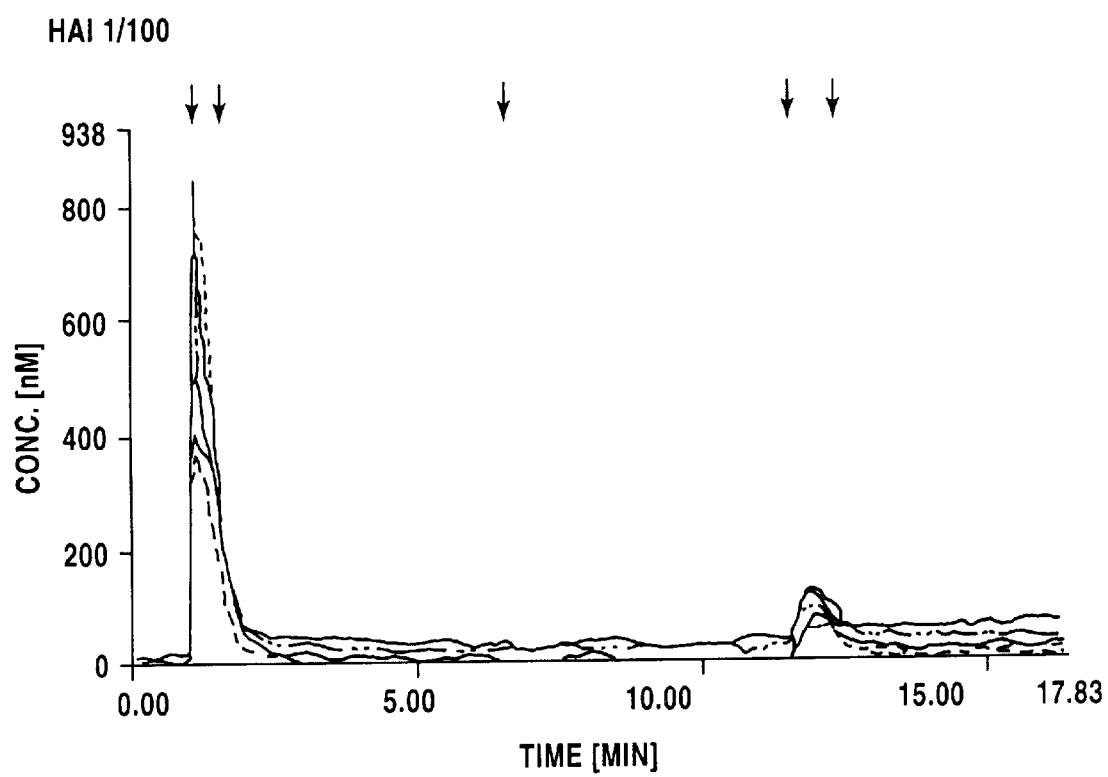
FIG. 6 is a graph showing the state of intruding calcium into cultured hippocampus cells of a rat with a 1/1000 solution of HAI for proving the effect of calcium channel antagonist.

In FIG. 6, the diluted 1/1,000 HAI solution was given to the cells between the first application of KCl and the second application of KCl. The second application of KCl was made in the presence of the diluted 1/1000 HAI solution. The increase of the calcium concentration by the second application of KCl was strongly suppressed. An average reaction with 10 cells in total was around 29% of the control.

Figure 7:
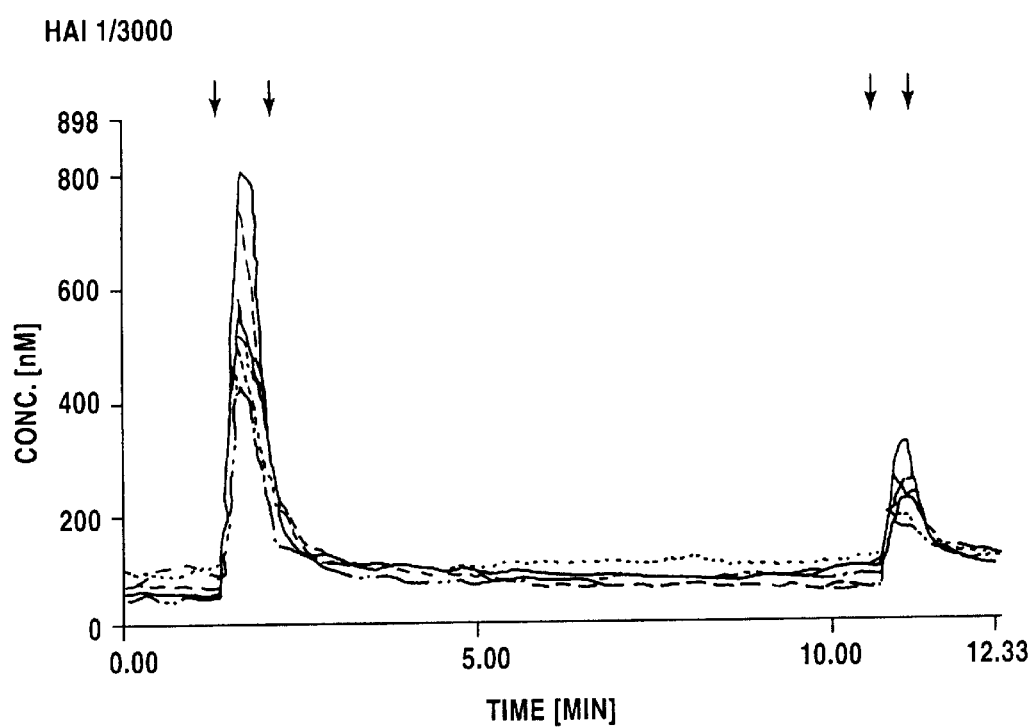
FIG. 7 is a graph showing the state of intruding calcium into cultured hippocampus cells of a rat with a 1/3000 solution of HAI for proving the effect of calcium channel antagonist.

In FIG. 7, the diluted 1/3000 HAI solution was given to the cells between the first application of KCl and the second application of KCl. The second application of KCl was made in the presence of the diluted 1/3000 HAI solution. The increase of the calcium concentration by the second application of KCl was considerably suppressed. An average reaction with 10 cells in total was about 57% of the control.

Figure 8:
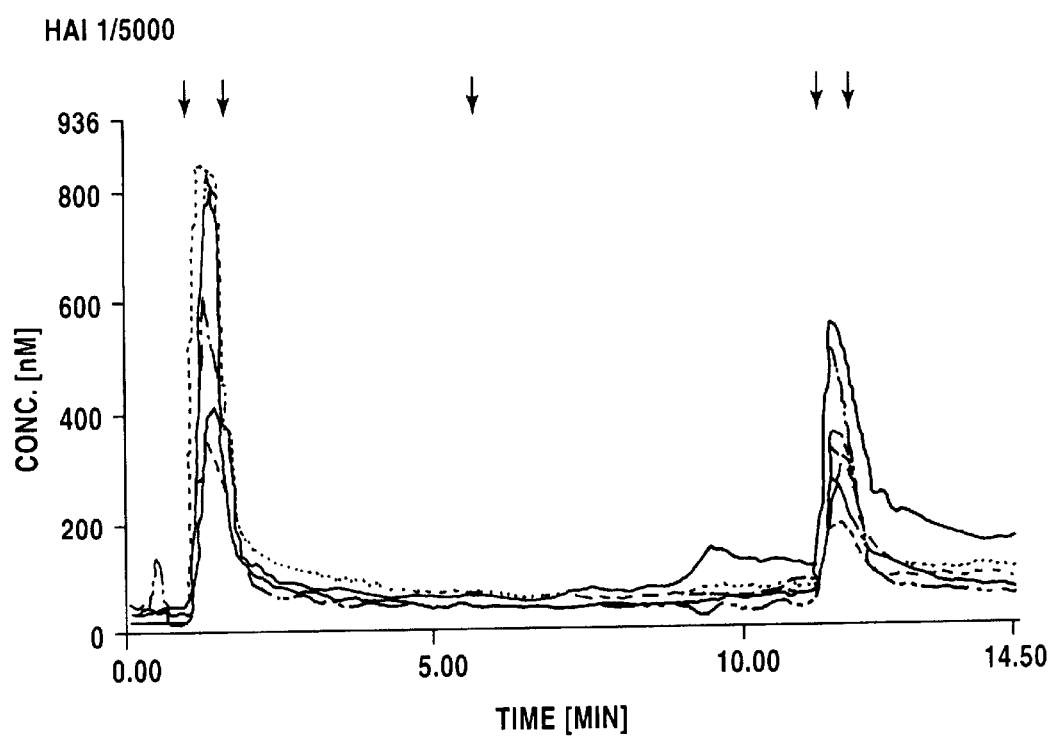
FIG. 8 is a graph showing the state of intruding calcium into cultured hippocampus cells of a rat with a 1/5000 solution of HAI for proving the effect of calcium channel antagonist.

In FIG. 8, the diluted 1/5000 HAI solution was given to the cells between the first application of KCl and the second application of KCl. The second application of KCl was made in the presence of the diluted 1/5000 HAI solution. The increase of the calcium concentration by the second application of KCl was considerably suppressed. An average reaction with 10 cells in total was about 82% of the control.

In view of the results of the foregoing Examples, it is understood that HAI serves to inhibit very strongly intrusion of calcium into the cultured hippocampus cells at the time of depolarization.

This fact apparently means that HAI promotes on one hand absorption of calcium in intestinal and inhibit on the other hand harmful intrusion of excess calcium in brain. Accordingly, these results proves manifestly that HAI prevents increase of the calcium concentration in cells by calcium paradox.

EFFECT OF INVENTION

According to the present invention, there is provided calcium channel antagonist (HAI) capable of inhibiting secretion of parathyroid hormones and also effective for promoting absorption and utilization of calcium when added to conventional calcium preparation,. It follows therefore that HAI provided by the present invention functions as a calcium channel antagonist which possesses an inhibitory action against intrusion of excess calcium to secure the mechanism of maintaining life while promoting absorption of calcium. This merit is especially desirable for senior persons desired to increase bone amount.

It is understood that the preceding Examples may be varied within the scope of the specification both as to the components and treating conditions by those skilled in the art to achieve essentially the same results.

As many widely different embodiments of this invention may be made without departing from the spirit and scope thereof, it is to be construed that the present invention is not limited to the specific embodiments thereof except as defined in the appended claims.

What is claimed is:

1. A calcium-containing preparation for inhibiting secretion of parathyroid hormones and promoting absorption and utilization of calcium, which comprises a calcium-containing extract obtained by extracting calcium from a calcium-containing material of plant origin with a sulfuric acid-containino solvent, and filtering the sulfuric acid-containing solvent.

2. A calcium-containing preparation according to claim 1, wherein the calcium-containing material of plant origin is at least one selected from the group consisting of sea weeds, beans, grasses belonging to Graminaceae, sesame, tea, and other mineral-containing plants.

3. A calcium-containing preparation according to claim 1 or 2, wherein the calcium-containing extract is diluted with an amount of water which is almost the same as the amount of calcium-containing extract.

* * * * *